US012636094B2

(12) United States Patent
Beck

(10) Patent No.: US 12,636,094 B2
(45) Date of Patent: May 26, 2026

(54) TECHNOLOGIES FOR MONITORING AND PREDICTING IMPACTION STATE OF AN ORTHOPAEDIC SURGICAL IMPLEMENT DURING AN ORTHOPAEDIC SURGICAL PROCEDURE

(71) Applicant: DePuy Synthes Products, Inc., Raynham, MA (US)

(72) Inventor: Clinton A. Beck, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 42 days.

(21) Appl. No.: 18/794,194

(22) Filed: Aug. 5, 2024

(65) Prior Publication Data

US 2024/0390081 A1     Nov. 28, 2024

Related U.S. Application Data

(63) Continuation of application No. 17/874,760, filed on Jul. 27, 2022, now Pat. No. 12,053,250, which is a
(Continued)

(51) Int. Cl.
*A61B 34/00* (2016.01)
*A61B 17/92* (2006.01)
(Continued)

(52) U.S. Cl.
CPC .............. *A61B 34/25* (2016.02); *A61B 17/92* (2013.01); *A61B 34/30* (2016.02); *G06N 3/08* (2013.01);
(Continued)

(58) Field of Classification Search
CPC ...................................................... A61B 34/25
See application file for complete search history.

(56) References Cited

U.S. PATENT DOCUMENTS 5,041,118 A * 8/1991 Wasilewski ........ A61B 17/1668
                                              606/85
10,905,456 B2 * 2/2021 Behzadi ................ A61F 2/4609
(Continued)

FOREIGN PATENT DOCUMENTS

DE    102006031356 A1    1/2008
EP       290375 A1    11/1988
(Continued)

OTHER PUBLICATIONS

International Preliminary Report on Patentability for International Application No. PCT/IB2021/050632, Aug. 11, 2022, 7 pages.
(Continued)

*Primary Examiner* — Christian A Sevilla
(74) *Attorney, Agent, or Firm* — Barnes & Thornburg LLP

(57) ABSTRACT

Technologies for monitoring impaction and predicting impaction state during an orthopaedic surgical procedure include one or more impaction sensors that generate sensor data. The surgical procedure includes impaction of an orthopaedic implement such as a surgical instrument or a prosthetic component. An impaction analyzer generates an impaction state prediction with a machine learning model based on the sensor data. The impaction state prediction may include an unseated state, a seated state, and a fracture state. An impaction state user interface outputs the impaction state prediction. A model trainer may train the machine learning model with labeled sensor data.

20 Claims, 5 Drawing Sheets

Related U.S. Application Data continuation of application No. 16/788,580, filed on Feb. 12, 2020, now Pat. No. 11,426,243.

(51) Int. Cl.
  *A61B 34/30* (2016.01)
  *G06N 3/08* (2023.01)

(52) U.S. Cl.
  CPC ..... *A61B 2017/922* (2013.01); *A61B 2562/02* (2013.01)

(56) References Cited

U.S. PATENT DOCUMENTS

| | | | | |
|---|---|---|---|---|
| 2004/0024311 A1* | 2/2004 | Quaid, III | ............. | A61B 90/39 |
| | | | | 600/428 |
| 2008/0125671 A1* | 5/2008 | Meneghini | ........... | A61F 2/4657 |
| | | | | 600/553 |
| 2015/0282856 A1 | 10/2015 | Haiat et al. | | |
| 2017/0367847 A1 | 12/2017 | Piriou et al. | | |
| 2018/0185167 A1* | 7/2018 | Rodgers | ................. | A61F 2/468 |
| 2019/0125293 A1* | 5/2019 | Behzadi | ................ | A61B 7/023 |
| 2019/0350726 A1 | 11/2019 | Behzadi | | |

FOREIGN PATENT DOCUMENTS

| | | |
|---|---|---|
| JP | 2018019813 A | 2/2018 |
| WO | 2019/141537 A1 | 7/2019 |

OTHER PUBLICATIONS

International Search Report for International Application No. PCT/IB2021/050632, Apr. 30, 2021, 6 pages.
Crisman A. et al., "Femoral Component Insertion Monitoring Using Human Cadaveric Specimens," Proceedings of the 25th IMAC Conference on Structural Dynamics, Orlando, FL, Jan. 2007.
Abou-Trabi D. et al., "Monitoring Femoral Component Insertion During Uncemented Total Hip Arthroplasty," Proceedings of the 24th International Modal Analysis Conference {IMAC), Sl. Louis, MO, Jan. 2006.
Japanese Office Action in JP2022-548698 drafted Nov. 28, 2024, 5 pages.

* cited by examiner

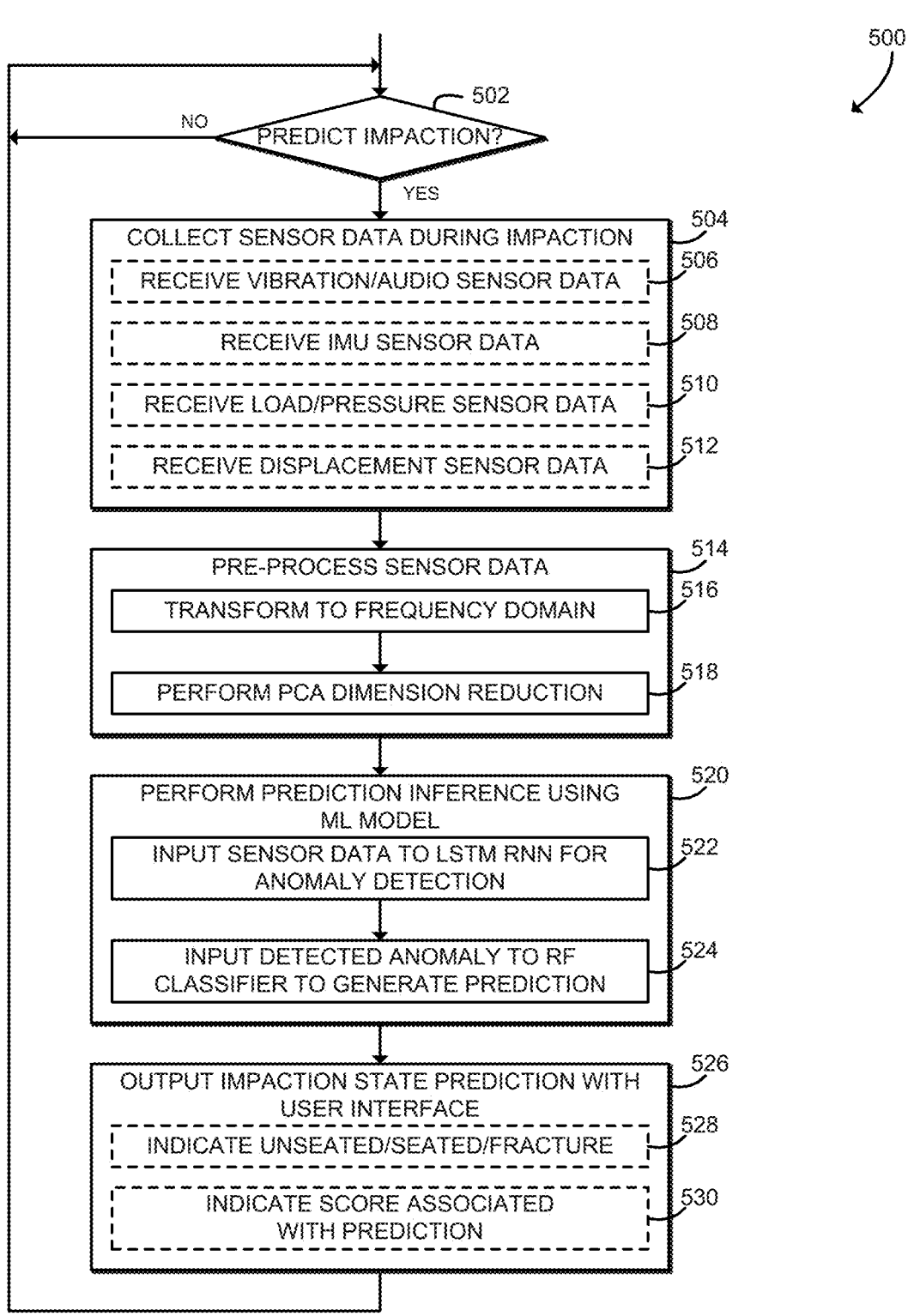

500

502

PREDICT IMPACTION?

NO

YES

COLLECT SENSOR DATA DURING IMPACTION — 504

RECEIVE VIBRATION/AUDIO SENSOR DATA — 506

RECEIVE IMU SENSOR DATA — 508

RECEIVE LOAD/PRESSURE SENSOR DATA — 510

RECEIVE DISPLACEMENT SENSOR DATA — 512

PRE-PROCESS SENSOR DATA — 514

TRANSFORM TO FREQUENCY DOMAIN — 516

PERFORM PCA DIMENSION REDUCTION — 518

PERFORM PREDICTION INFERENCE USING ML MODEL — 520

INPUT SENSOR DATA TO LSTM RNN FOR ANOMALY DETECTION — 522

INPUT DETECTED ANOMALY TO RF CLASSIFIER TO GENERATE PREDICTION — 524

OUTPUT IMPACTION STATE PREDICTION WITH USER INTERFACE — 526

INDICATE UNSEATED/SEATED/FRACTURE — 528

INDICATE SCORE ASSOCIATED WITH PREDICTION — 530

FIG. 5

TECHNOLOGIES FOR MONITORING AND PREDICTING IMPACTION STATE OF AN ORTHOPAEDIC SURGICAL IMPLEMENT DURING AN ORTHOPAEDIC SURGICAL PROCEDURE

CROSS-REFERENCE TO RELATED APPLICATION

The present application is a continuation of, and claims priority to, U.S. application Ser. No. 17/874,760, now U.S. Pat. No. 12,053,250, entitled "TECHNOLOGIES FOR MONITORING AND PREDICTING IMPACTION STATE OF AN ORTHOPAEDIC SURGICAL IMPLEMENT DURING AN ORTHOPAEDIC SURGICAL PROCEDURE," which is a continuation of U.S. application Ser. No. 16/788,580, now U.S. Pat. No. 11,426,243, entitled "TECHNOLOGIES FOR MONITORING AND PREDICTING IMPACTION STATE OF AN ORTHOPAEDIC SURGICAL IMPLEMENT DURING AN ORTHOPAEDIC SURGICAL PROCEDURE," which was filed on Feb. 12, 2020, the entirety of both of which is incorporated herein by reference.

TECHNICAL FIELD

The present disclosure relates generally to orthopaedic surgical tools and systems and, more particularly, to technologies for monitoring and predicting impaction state of an orthopaedic surgical implement during an associated orthopaedic surgical procedure.

BACKGROUND

Joint arthroplasty is a well-known surgical procedure by which a diseased and/or damaged natural joint is replaced by a prosthetic joint, which may include one or more orthopaedic implants. For example, in a hip arthroplasty surgical procedure, a patient's natural hip ball and socket joint is partially or totally replaced by a prosthetic hip joint. A typical prosthetic hip joint includes an acetabular cup component and a femoral head component. An acetabular cup component generally includes an outer shell configured to engage the acetabulum of the patient and an inner bearing or liner coupled to the shell and configured to engage the femoral head. The femoral head component and inner liner of the acetabular component form a ball and socket joint that approximates the natural hip joint. Similarly, in a knee arthroplasty surgical procedure, a patient's natural knee joint is partially or totally replaced by a prosthetic knee joint.

To facilitate the replacement of the natural joint with a prosthetic joint, orthopaedic surgeons may use a variety of orthopaedic surgical instruments such as, for example, reamers, broaches, drill guides, drills, positioners, insertion tools and/or other surgical instruments. For example, a surgeon may prepare a patient's femur to receive a femoral component by impacting a femoral broach into the patient's surgically prepared femur until the broach is sufficiently impacted or seated into the patient's surrounding bony anatomy.

One type of orthopaedic implants that may be used to replace a patient's joint are known as cementless orthopaedic implants. Cementless implants are implanted into a patient's boney anatomy by impacting the implant into a corresponding bone of the patient. For example, a cementless acetabular prosthesis typically includes an acetabular cup outer shell, which is configured to be implanted into a patient's acetabulum. To do so, an orthopaedic surgeon impacts the outer shell into the patient's acetabulum until the outer shell is sufficiently seated into the patient's surrounding bony anatomy. Similarly, in other arthroplasty surgical procedures such as knee arthroplasty surgical procedures, an orthopaedic surgeon strives for proper seating of the corresponding orthopaedic implant.

Typically, orthopaedic surgeons rely on experience and tactile and auditory feedback during the surgical procedure to determine when the surgical instrument and/or the orthopaedic implant is sufficiently impacted or seated into the patient's boney anatomy. For example, the surgeon may rely on tactile sensations felt through an impactor or inserter tool while the surgeon hammers the surgical tool with an orthopaedic mallet to impact the implant or instrument into the patient's boney anatomy. However, solely relying on such environmental feedback can result in the under or over impaction of the orthopaedic instrument or implant into the patient's bone. Over-impaction can result in fracture of the patient's corresponding bone, while under-impaction can result in early loosening of the orthopaedic implant.

SUMMARY

According to one aspect, a system for predicting impaction state during an orthopaedic surgical procedure includes one or more impaction sensors to generate sensor data indicative of impaction state of an orthopaedic implement relative to a patient's bone, an impaction data collector to collect the sensor data during the orthopaedic surgical procedure from the impaction sensor, an impaction analyzer to generate an impaction state prediction with a machine learning model based on the sensor data, wherein the impaction state prediction includes an unseated state, a seated state, or a fracture state, and an impaction state user interface to output the impaction state prediction. In an embodiment, the orthopaedic implement includes a femoral broach or a prosthetic component.

In an embodiment, the system further includes a surgical instrument impaction handle. The one or more impaction sensors include a vibration sensor coupled to the impaction handle, an inertial measurement unit coupled to the impaction handle, and an external microphone.

In an embodiment, to generate the impaction state prediction with the machine learning model based on the sensor data includes to pre-process the sensor data to generate processed sensor data, and input the processed sensor data to the machine learning model. In an embodiment, to pre-process the sensor data includes to transform the sensor data to a frequency domain to generate frequency domain sensor data, and reduce dimensionality of the frequency domain sensor data to generate the processed sensor data.

In an embodiment, to generate the impaction state prediction with the machine learning model based on the sensor data includes to input the sensor data to a recurrent neural network to generate anomaly prediction data, and input the anomaly prediction data to a classifier to generate the impaction state prediction. In an embodiment, the recurrent neural network includes a long short-term memory network, and the classifier includes a random forest predictive model.

In an embodiment, the system further includes a computing device that includes the one or more impaction sensors, the impaction data collector, the impaction analyzer, and the impaction state user interface. The one or more impaction sensors includes a microphone of the computing device, and the impaction state user interface includes a display screen of the computing device.

According to another aspect, one or more non-transitory, machine-readable media include a plurality of instructions that, in response to execution, cause one or more processors to collect sensor data during an orthopaedic surgical procedure from an impaction sensor, wherein the sensor data is indicative of impaction state of an orthopaedic implement relative to a patient's bone; generate an impaction state prediction with a machine learning model based on the sensor data, wherein the impaction state prediction includes an unseated state, a seated state, or a fracture state; and output the impaction state prediction.

In an embodiment, to collect the sensor data from the impaction sensor includes to collect vibration data from a vibration sensor coupled to a surgical instrument; collect motion data from an inertial measurement unit coupled to the surgical instrument; and collect audio data from an external microphone.

In an embodiment, to generate the impaction state prediction with the machine learning model based on the sensor data includes to pre-process the sensor data to generate processed sensor data; and input the processed sensor data to the machine learning model.

In an embodiment, to generate the impaction state prediction with the machine learning model based on the sensor data includes to input the sensor data to a recurrent neural network to generate anomaly prediction data; and input the anomaly prediction data to a classifier to generate the impaction state prediction. In an embodiment, the recurrent neural network includes a long short-term memory network, and the classifier includes a random forest predictive model.

According to another aspect, one or more non-transitory, machine-readable media include a plurality of instructions that, in response to execution, cause one or more processors to collect sensor data from an impaction sensor, wherein the sensor data is indicative of impaction state of an orthopaedic implement relative to a bone or bone analog; label the sensor data with an impaction state label to generate labeled sensor data, wherein the impaction state label includes an unseated state, a seated state, or a fracture state; and train a machine learning model to predict impaction state for input sensor data based on the labeled sensor data.

In an embodiment, to train the machine learning model based on the labeled sensor data includes to pre-process the labeled sensor data to generate processed sensor data; and train the machine learning model based on the processed sensor data. In an embodiment, to pre-process the labeled sensor data includes to transform the labeled sensor data to a frequency domain to generate frequency domain sensor data; and reduce dimensionality of the frequency domain sensor data to generate the processed sensor data. In an embodiment, to reduce the dimensionality of the frequency domain sensor data includes to perform principal component analysis of the frequency domain sensor data.

In an embodiment, to train the machine learning model to predict impaction state for input sensor data based on the labeled sensor data includes to train a recurrent neural network with the labeled sensor data to identify anomalies in the labeled sensor data; and train a classifier with the anomalies in the labeled sensor data to predict the impaction state. In an embodiment, the recurrent neural network includes a long short-term memory network. In an embodiment, the classifier includes a random forest predictive model.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which:

FIG. 5 is a simplified flow diagram of a method for monitoring and predicting impaction state of an orthopaedic surgical implement that may be executed by the system of FIGS. 1-3.

DETAILED DESCRIPTION OF THE DRAWINGS

Figure 1:
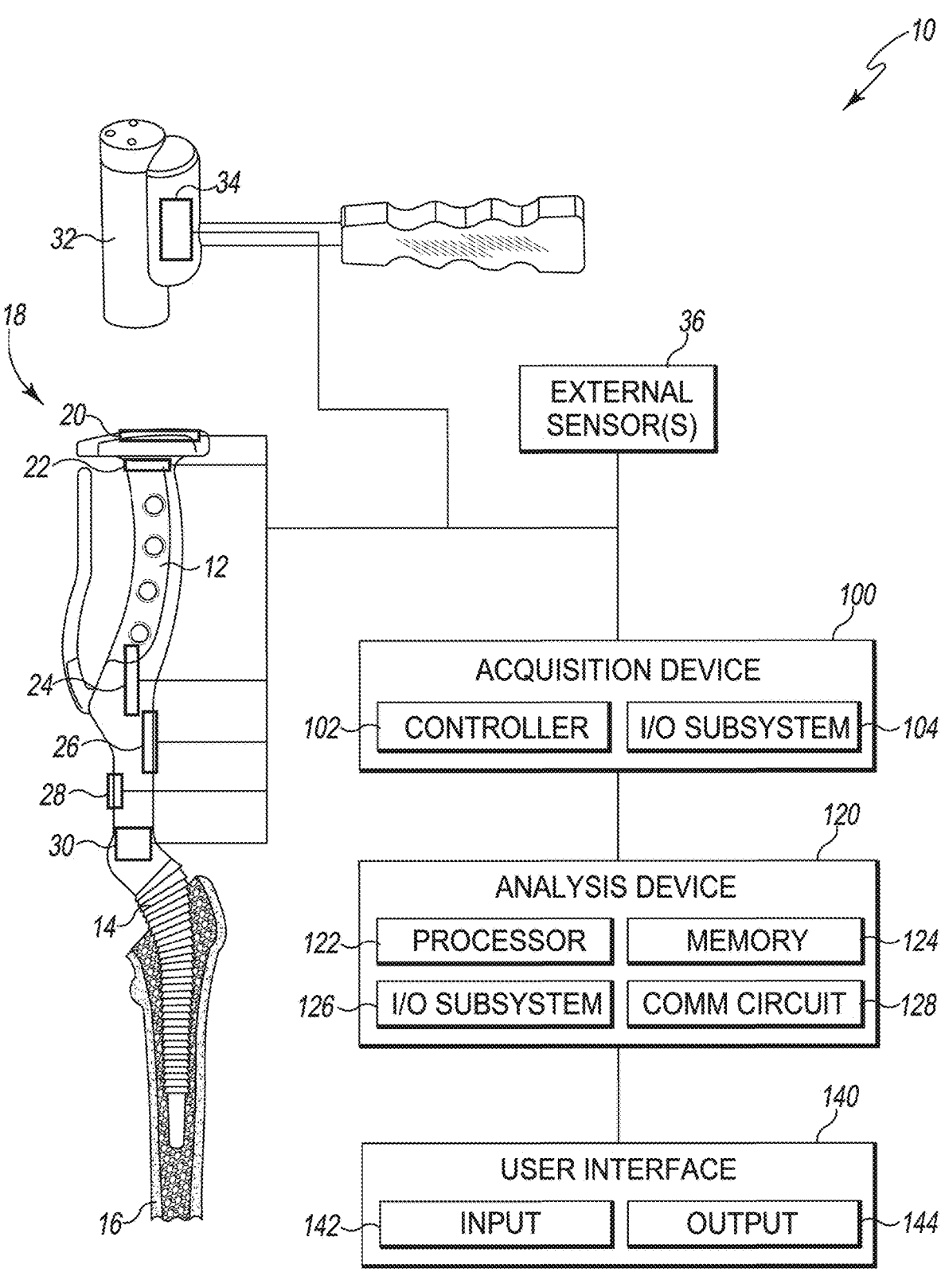
FIG. 1 is a schematic diagram of a system for monitoring and predicting impaction state of an orthopaedic surgical implement in use during an orthopaedic surgical procedure.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a surgical instrument system 10 is used during an orthopaedic surgical procedure, which is shown illustratively as a total hip arthroplasty (THA) procedure. During that procedure, an orthopaedic surgeon impacts a surgical broach 14 into a patient's femur 16 by striking an instrument handle 12 that is attached to the broach 14 using an orthopaedic mallet 32 (or other impactor). As the surgeon strikes the handle 12, an acquisition device 100 captures sensor data from multiple sensors in the operating environment, including sensors attached to the handle 12 and/or the mallet 32 and/or external sensors. The acquisition device 100 provides the sensor data to an analysis device 120, which uses a machine learning model to generate a prediction of the impaction state of the broach 14 based on the sensor data. In the illustrative embodiment, the impaction state is defined as being one of unseated (i.e., the broach 14 is not seated in the femur 16), seated (i.e., the broach 14 is firmly seated in the femur 16), or fracture (i.e., the femur 16 has fractured). A user interface 140 outputs the prediction, which provides feedback on the impaction state to the surgeon. Thus, the system 10 may aid the surgeon in determining when the broach 14 is firmly seated as well as identifying and preventing proximal femoral fractures during THA surgeries.

Additionally, although described as involving impacting a femoral broach 14, it should be understood that the concepts of the present disclosure may apply to other orthopaedic implements and other orthopaedic procedures. Orthopaedic implements may include orthopaedic surgical instruments such as broaches and trial components, as well as prosthetic components. For example, the concepts of the present disclosure may also apply to impacting cementless orthopaedic implants such as a cementless acetabular cup outer shell.

As shown in FIG. 1, the broach 14 includes an outer surface having a plurality of cutting teeth formed thereon. The broach 14 is configured to shape the intramedullary canal of the patient's femur 16 to receive a femoral component (not shown). The broach 14 is formed from a metallic material, such as, for example, stainless steel or cobalt chromium. A proximal end of the broach 14 includes a mounting post or other mounting bracket that may be attached to the instrument handle 12.

The instrument handle 12 is also formed from a metallic material, such as, for example, stainless steel or cobalt chromium, and includes an elongated body that extends from a mounting tip to a strike plate. The mounting tip is configured to attach to the broach 14, and in some embodiments may also be configured to attach to one or more other surgical instruments and/or orthopaedic implants. The instrument handle 12 includes a grip configured to receive the hand of a surgeon or other user to allow the user to manipulate the handle 12. The strike plate of the handle 12 includes a durable surface suitable for use with a striking tool such as the orthopaedic mallet 32.

The instrument handle 12 also includes or is otherwise coupled to a number of impaction sensors 18. As described further below, the impaction sensors 18 are configured to generate sensor data that is indicative of the impaction state of the broach 14 relative to the patient's femur 16. Illustratively, the impaction sensors 18 include a force sensing resistor (FSR) and/or load cell 20, a thermometer 22, a vibration sensor 24, a displacement sensor 26, an inertial measurement unit (IMU) sensor 28, and an audio sensor 30.

The FSR 20 and/or the load cell 20 measure the force exerted on the strike plate of the instrument handle 12 by the orthopaedic mallet 32. An FSR sensor may be embodied as a polymer sheet or film with a resistance that varies based on the applied force or pressure. Similarly, a load cell may be embodied as a transducer that converts force into an electrical output that may be measured. In some embodiments, the handle 12 may include one or both of an FSR and/or a load cell.

The thermometer 22 measures temperature of the instrument handle 12 and/or temperature of the surgical environment. The thermometer 22 may be embodied as a digital temperature sensor, a thermocouple, or other temperature sensor.

The vibration sensor 24 measures vibration in the handle 12 during impaction in the form of pressure, acceleration, and force on the handle 12. The vibration sensor 24 may be embodied as a piezoelectric vibration sensor or other electronic vibration sensor. A piezoelectric sensor uses the piezoelectric effect to measure changes in pressure, acceleration, strain, or force, by converting those quantities to electric charge.

The displacement sensor 26 measures the position and/or change in position of the broach 14 relative to the femur 16. The displacement sensor 26 may be embodied as an optical time-of-flight sensor, which senses distance by measuring the amount of time required for an infrared laser emitted by the sensor 26 to reflect off of a surface back to the displacement sensor 26. The displacement sensor 26 may measure the distance moved by the broach 14 into the patient's femur 16 for each strike of the orthopaedic mallet 32.

The IMU sensor 28 measures and reports motion data associated with the instrument handle 12, including the specific force/acceleration and angular rate of the instrument handle 12, as well as the magnetic field surrounding the instrument handle 12 (which may be indicative of global orientation). The IMU sensor 28 may be embodied as or otherwise include a digital accelerometer, gyroscope, and magnetometer per axis of motion. The illustrative IMU sensor 28 is embodied as a nine degrees of freedom IMU (e.g., capable of measuring linear acceleration, angular acceleration, and magnetic field in each of three axes).

The audio sensor 30 measures sound signals generated during impaction of the broach 14. The audio sensor 30 may be embodied as a microphone, digital-to-analog converter, or other acoustic to electric transducer or sensor.

As shown in FIG. 1, the orthopaedic mallet 32 includes a handle and a mallet head connected to the handle via a shaft. As with a typical hammer or mallet, the orthopaedic surgeon may grasp the mallet 32 by the handle and swing the mallet 32 to cause impaction of the mallet head with the instrument handle 12 (or other structure). The orthopaedic mallet 32 further includes an IMU sensor 34, which measures motion data including the acceleration, angular rate, and magnetic field of the mallet 32. Although only one IMU sensor 34 is shown in FIG. 1, it should be appreciated that the orthopaedic mallet 32 may include additional impaction sensors 18 in other embodiments, similar to the instrument handle 12. In such embodiments, the multiple impaction sensors 18 may be similar or of different types.

In some embodiments, the orthopaedic mallet 32 may be embodied as an automated impactor (not shown), rather than a manual mallet. For example, the automated impactor may be embodied as a Kincise™ surgical automated system component commercially available from DePuy Synthes of Warsaw, Indiana. In such embodiments, the automated impactor may include an IMU sensor 34 and/or other impaction sensors 18. Similarly, in some embodiments, the orthopaedic mallet 32 may be embodied as a dynamic impulse hammer that measures force exerted on the handle 12 as the hammer tip strikes the handle 12.

The system 10 may also include one or more external impaction sensors 36, which are not located on either the instrument handle 12 or the orthopaedic mallet 32. The external impaction sensor(s) 36 may be embodied any type of sensor capable of producing sensor data indicative of impaction of the broach 14, even though the sensors 36 are not in physical contact with either the instrument handle 12 or the orthopaedic mallet 32. For example, in an embodiment, the external impaction sensor 36 includes an audio sensor (e.g., a microphone) capable of generating audio sensor data indicative of impaction between the instrument handle 12 and the orthopaedic mallet 32, an image sensor (e.g., a camera) capable of generating image data indicative of impaction between the instrument handle 12 and the orthopaedic mallet 32, and/or other sensors capable of generating data indicative of impaction between the instrument handle 12 and the orthopaedic mallet 32.

Although illustrated as including impaction sensors 18 coupled to the instrument handle 12, impaction sensor 34 coupled to the orthopaedic mallet 32, and external sensors 36, it should be understood that in some embodiments the system 10 may include a different number and/or arrangement of sensors 18, 34, 36. For example, in an embodiment, the system 10 may include a vibration sensor 24 and an IMU sensor 28 coupled to the handle 12 and an external microphone 36. Thus, in those embodiments, one or more components of the system 10 (e.g., the orthopaedic mallet 32) may be embodied as typical orthopaedical tools and include no electronic components.

As shown in FIG. 1, the sensors 18, 34, 36 are coupled to the acquisition device 100, which may be embodied as a single device such as a multi-channel data acquisition system, a circuit board, an integrated circuit, an embedded system, a field-programmable-array (FPGA), a system-on-a-chip (SOC), or other integrated system or device. In the illustrative embodiment, the acquisition device 100 includes a controller 102 and an input/output (I/O) subsystem 104. The controller 102 may be embodied as any type of controller or other processor capable of performing the functions described herein. For example, the controller 102 may be embodied as a microcontroller, a digital signal processor, a single or multi-core processor(s), discrete compute circuitry, or other processor or processing/controlling circuitry. The acquisition device 100 may also include volatile and/or non-volatile memory or data storage capable of storing data, such as the sensor data produced by the impaction sensors 18, 34, 36.

The acquisition device 100 is communicatively coupled to other components of the system 10 via the I/O subsystem 104, which may be embodied as circuitry and/or components to facilitate input/output operations with the controller 102 and other components of the system 10. For example, the I/O subsystem 104 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

As shown, the acquisition device 100 is communicatively coupled to the analysis device 120, which may be embodied as any type of device or collection of devices capable of performing various compute functions and the functions described herein, such as a desktop computer, a workstation, a server, a special-built compute device, a mobile compute device, a laptop computer, a tablet computer, or other computer or compute device. In the illustrative embodiment, the analysis device 120 includes a processor 122, a memory 124, an I/O subsystem 126, and a communication circuit 128. The processor 122 may be embodied as any type of processor capable of performing the functions described herein. For example, the processor 122 may be embodied as a single or multi-core processor(s), a digital signal processor, a microcontroller, discrete compute circuitry, other processor or processing/controlling circuitry. Similarly, the memory 124 may be embodied as any type of volatile and/or non-volatile memory or data storage capable of storing data, such as the sensor data received from the acquisition device 100 and/or model data as described further below. The analysis device 120 may also include other components commonly found in a compute device, such as a data storage device and various input/output devices (e.g., a keyboard, mouse, display, etc.). Additionally, although illustrated as a single device, it should be understood that in some embodiments, the analysis device 120 may be formed from multiple computing devices distributed across a network, for example operating in a public or private cloud.

The analysis device 120 is communicatively coupled to other components of the system 10 via the I/O subsystem 126, which may be embodied as circuitry and/or components to facilitate input/output operations with the analysis device 120 (e.g., with the processor 122 and/or the memory 124) and other components of the system 10. For example, the I/O subsystem 126 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The communication circuit 128 is configured to communicate with external devices such as the acquisition device 100, the user interface 140, other analysis devices 120, and/or other remote devices. The communication circuit 128 may be embodied as any type of communication circuits or devices capable of facilitating communications between the analysis device 120 and other devices. To do so, the communication circuit 128 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

The user interface 140 may be embodied as a collection of various output and/or input devices to facilitate communication between the system 10 and a user (e.g., an orthopaedic surgeon). Illustratively, the user interface 140 includes one or more output devices 144 and/or one or more input devices 142. Each of the output devices 144 may be embodied as any type of output device capable of providing a notification or other information to the orthopaedic surgeon or other user. For example, the output devices 144 may be embodied as visual, audible, or tactile output devices. In the illustrative embodiment, the user interface 140 includes one or more visual output devices, such as a light emitting diode (LED), a light, a display screen, or the like. Each of the input devices 142 may be embodied as any type of input device capable of control or activation by the orthopedic surgeon to provide an input, data, or instruction to the system 10. For example, the input devices 142 may be embodied as a button (e.g., an on/off button), a switch, a touchscreen display, or the like.

Although illustrated as including a separate acquisition device 100, analysis device 120, and user interface 140, it should be understood that in some embodiments one or more of those devices may be incorporated into the same device and/or other components of the system 10. For example, in some embodiments, the functionality of the acquisition device 100 and the analysis device 120 may be combined in a single computing device. Additionally or alternatively, the functionality of the user interface 140 may also be combined with the analysis device 120. In some embodiments, the user interface 140 may be combined with otherwise included with one or more surgical instruments, such as the instrument handle 12 and/or the orthopaedic mallet 32. Further, in some embodiments the analysis device 120 may be coupled directly to one or more sensors, such as the IMU 34 and/or an external sensor 36, without use of the acquisition device 100.

In some embodiments, functionality of an external sensor 36, the acquisition device 100, the analysis device 120, and the user interface 140 may be combined in a single computing device. For example, a tablet computer may include a microphone or other external sensor 36. Continuing that example, the tablet computer may capture sensor data from the microphone 36, use the machine learning model to generate a prediction of the impaction state of the broach 14 based on the sensor data, and output the prediction using a display screen of the tablet computer.

Figure 2:
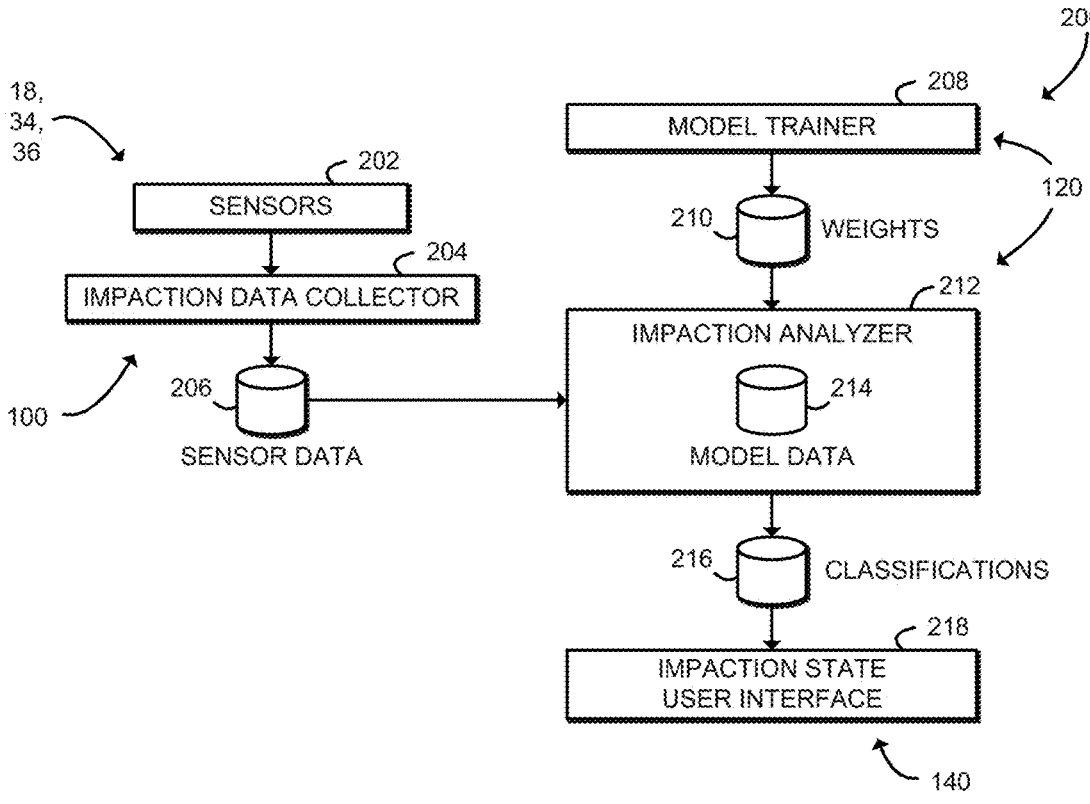
FIG. 2 is a simplified block diagram of an environment that may be established by the system of FIG. 1.

Referring now to FIG. 2, in an illustrative embodiment, the system 10 establishes an environment 200 during operation. The illustrative environment 200 includes sensors 202, an impaction data collector 204, a model trainer 208, an impaction analyzer 212, and an impaction state user interface 218. The various components of the environment 200 may be embodied as hardware, firmware, software, or a combination thereof. As such, in some embodiments, one or more of the components of the environment 200 may be embodied as circuitry or collection of electrical devices (e.g., the sensors 18, 34 36, the acquisition device 100, the analysis device 120, and/or the user interface 140). For example, in the illustrative embodiment, the sensors 202 may be embodied as the sensors 18, 34, 36, the impaction data collector 204 may be embodied as the acquisition device 100, the model trainer 208 and the impaction analyzer 212 may be embodied as the analysis device 120, and the impaction state user interface 218 may be embodied as the user interface 140. Additionally, in some embodiments, one or more of the illustrative components may form a portion of another component and/or one or more of the illustrative components may be independent of one another.

The sensors 202 are configured to generate sensor data indicative of impaction state of an orthopaedic implement relative to a patient's bone. For example, the sensors 202 may include the vibration sensor 24, the IMU 28, and/or the external microphone 36. The impaction data collector 204 is configured to collect the sensor data during the orthopaedic surgical procedure from the impaction sensors 202. The impaction data collector 204 provides the collected sensor data 206 to the impaction analyzer 212.

The impaction analyzer 212 is configured to generate an impaction state prediction with a machine learning model based on the sensor data 206. The impaction state prediction includes classifications 216 of the sensor data 206. The classifications 216 include an unseated state, a seated state, or a fracture state. In some embodiments, the impaction state prediction may also include a probability or other relative score. The impaction analyzer 212 may store model data 214 related to the machine learning model, including historical data, model weights, decision trees, and other model data 214.

The impaction state user interface 218 is configured to output the impaction state prediction. Outputting the impaction state prediction may include displaying a visual representation of the impaction state prediction, outputting an auditory indication or warning of the impaction state prediction, or otherwise outputting the impaction state prediction.

The model trainer 208 is configured to label the collected sensor data 206 with an impaction state label to generate labeled sensor data. Similar to the impaction state prediction, the impaction state label includes an unseated state, a seated state, or a fracture state. The model trainer 208 is further configured to train the machine learning model of the impaction analyzer 212 to predict impaction state for input sensor data 206 based on the labeled sensor data 206. The model trainer 208 may train the machine learning model by providing and/or modifying weights 210 associated with the machine learning model.

Figure 3:
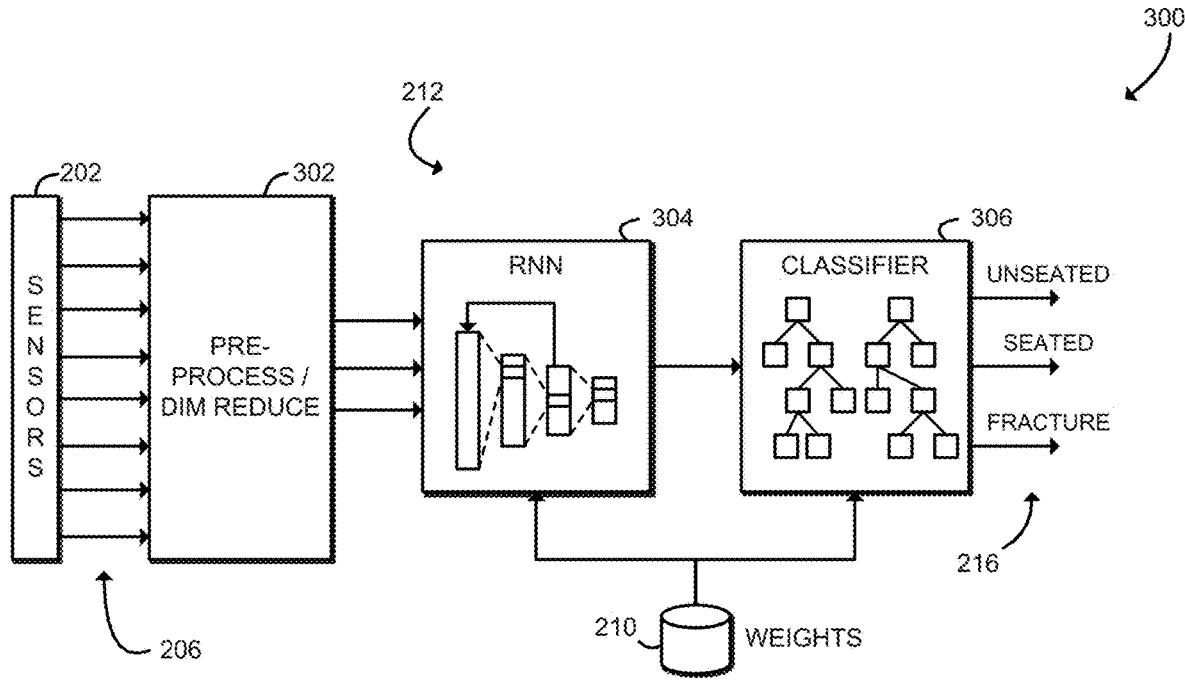
FIG. 3 is a simplified block diagram of a machine learning model of an impaction analyzer of the system of FIGS. 1-2.

Referring now to FIG. 3, diagram 300 illustrates one potential embodiment of a machine learning model that may be established by the impaction analyzer 212. As shown, the sensor data 206 is input to a pre-processing/dimensionality reduction stage 302. The pre-processing stage 302 may, for example, transform the sensor data 206 to a frequency domain to generate frequency domain sensor data, and then reduce dimensionality of the frequency domain sensor data to generate the processed sensor data. The pre-processing stage 302 may reduce dimensionality using a principal component analysis procedure.

As shown, the processed sensor data is input to a recurrent neural network (RNN) 304. The RNN 304 is illustratively a long short-term memory (LSTM) that has been trained to identify anomalies in the processed sensor data. Anomaly detection is the identification of data points, items, observations or events that do not conform to the expected pattern of a given group. These anomalies may occur infrequently but may signify a large and/or otherwise significant occurrence. Illustratively, the detected anomalies include the broach 14 being in a fully seated condition and a fracture of the femur 16.

Output from the RNN 304 is passed to a classifier 306. The classifier 306 is illustratively a random forest (RF) predictive model. The classifier 306 generates the classifications 216 based on the output from the RNN 304. The classifications 216 indicate whether the impaction state is predicted to be unseated, seated, or fracture, and in some embodiments may include a probability or other relative score. Of course, it should be appreciated that other machine learning models may be used in other embodiments.

Figure 4:
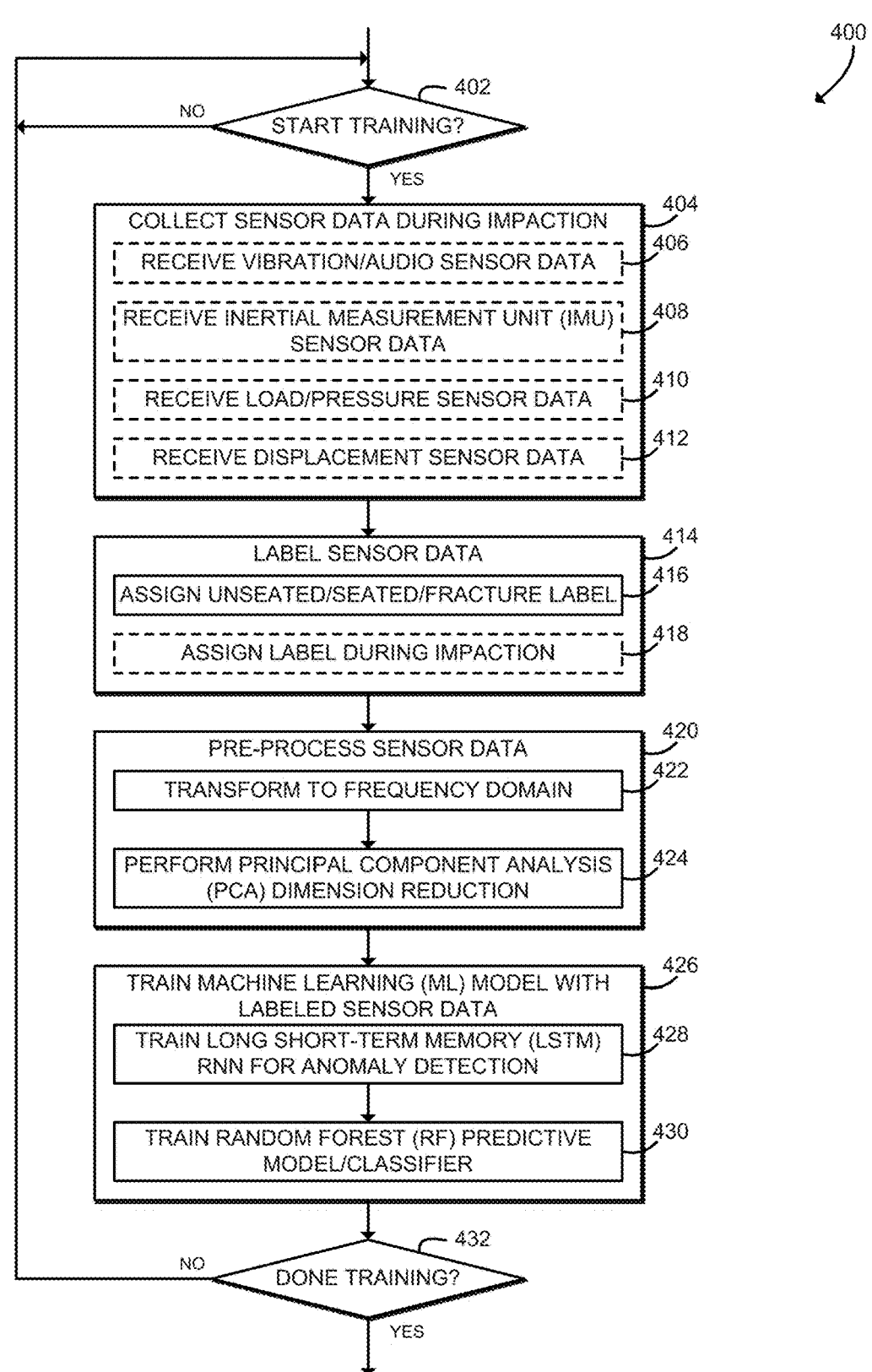
FIG. 4 is a simplified flow diagram of a method for training the machine learning model that may be executed by the system of FIGS. 1-3.

Referring now to FIG. 4, in use, the instrument system 10 may perform a method 400 for training the machine learning model of the impaction analyzer 212. For example, the operations of the method 400 may be performed by one or more components of the environment 200 described above in connection with FIG. 2. The method 400 begins with block 402, in which the system 10 determines whether to start training. For example, a surgeon or other operator may instruct the system 10 to start training using the user interface 140 or other control. If the system 10 determines to start training, the method 400 advances to block 404. If not, the method 400 loops back to block 402.

In block 404, the acquisition device 100 collects sensor data from one or more sensors 18, 34, and/or 36 during impaction of the broach 14 into the patient's femur 16. As described above, during an orthopaedic surgical procedure, the surgeon impacts the broach 14 into the patient's femur 16 by striking the instrument handle 12 attached to the broach 14 using the orthopaedic mallet 32. The acquisition device 100 captures sensor signals, including acceleration, vibration, and acoustic signals, as the surgeon impacts the instrument handle 12. The sensor data may be captured during an orthopaedic surgical procedure or during a testing procedure or other data gathering operation. In a testing procedure, the surgeon or other operator may impact the broach 14 into a replicate femur or other bone analog. The surgeon may strike the instrument handle 12 in different locations on the strike plate and/or at different angles. As described further below, the machine learning model may be trained to recognize sensor data associated with impacts at different locations and/or at different impaction angles. After collecting the sensor data, the acquisition device 100 provides the sensor data to the analysis device 120 for further processing.

In some embodiments, in block 406 the acquisition device 100 receives vibration and/or audio sensor data. In the illustrative embodiment, the acquisition device 100 receives vibration data from the vibration sensor 24 coupled to the instrument handle 12 and audio data from an external audio sensor 36. Additionally or alternatively, in some embodiments the acquisition device 100 may receive audio data from an audio sensor 30 coupled to the instrument handle 12.

In some embodiments, in block 408 the acquisition device 100 receives IMU sensor data. In the illustrative embodiment, the acquisition device 100 receives IMU data (indicative of motion, including linear acceleration, angular rate, and magnetic field) from the IMU sensor 28 coupled to the instrument handle 12. Additionally or alternatively, in some embodiments the acquisition device 100 may receive IMU data from an IMU sensor coupled to the orthopaedic mallet 32.

In some embodiments, in block 410, the acquisition device 100 receives load or pressure data from the FSR/load cell 20 coupled to the instrument handle 12. In some embodiments, in block 412 the acquisition device 100 receives displacement data from the displacement sensor 26 coupled to the instrument handle 12.

In block 414, the analysis device 120 (or in some embodiments the acquisition device 100) labels the collected sensor data. Labeling the sensor data allows the received sensor data to be used for training the machine learning model as described further below. The sensor data may be labeled by an operator of the system 10, for example by selecting an appropriate label using the user interface 140.

In block 416, a label of unseated, seated, or fracture is assigned to each data point or group of data points of the sensor data. Unseated indicates that the broach 14 is not fully seated in the femur 16. In the unseated state, the broach 14 is loose inside the femur 16 and has low motion resistance and low rotational stability. In the unseated state, the femur 16 has a low fracture risk. Seated indicates that the broach 14 is firmly seated in the femur 16 and does not progress with impaction. In the seated state, the broach 14 is firmly seated inside the femur 16 and has high motion resistance and high rotational stability. In the seated state, the femur 16 has a high risk of fracture with further impaction. Fracture indicates that the femur 16 has a fracture (e.g., a fracture in the calcar and/or proximal femur) in one or more locations. In the fracture state, the broach 14 may be well seated and resistant to attempted motion. Further impaction in the fracture state may worsen the fracture.

In some embodiments, in block 418, the label may be assigned to the sensor data during impaction. For example, a surgeon or other operator may input the label using the user interface 140 during the impaction procedure. As another example, the label may be pre-assigned for a series of impactions in a test procedure. Continuing that example, in the test procedure a replicate femur may be pre-fractured prior to performing the test procedure. In that example, all sensor data collected during the test using the pre-fractured replicate femur may be labeled as fracture.

In block 420, the analysis device 120 pre-processes the sensor data to prepare for input to the machine learning model. The analysis device 120 may perform one or more filtering, normalization, and/or feature extraction processes to prepare the sensor data for processing. In block 422, the analysis device 120 transforms the sensor data (collected as time series data) into frequency domain data using a fast Fourier transform (FFT). Transforming to frequency domain may remove noise and allow for improved identification of peaks in the sensor data. In block 424, the analysis device 120 performs principal component analysis to reduce dimensionality of the sensor data. Reducing dimensionality may improve processing efficiency by combining and/or eliminating dependent variables in the sensor data. It should be understood that in some embodiments, the system 10 may not reduce dimensionality of the sensor data, and instead, for example, may reduce the volume of input sensor data by removing certain sensors from the system 10.

In block 426, the analysis device 120 trains the machine learning model with the labeled data. The machine learning model is trained to identify anomalies in the sensor data, including the broach 14 being fully seated in the femur 16 and a fracture of the femur 16. The machine learning model is further trained to classify the sensor data, based on any identified anomalies, into the unseated, seated, and fracture states. The analysis device 120 may train the machine learning model using any appropriate training algorithm. In block 428, the analysis device 120 trains a long short-term memory (LSTM) recurrent neural network to detect anomalies based on the labeled sensor data. The LSTM model may be trained using a gradient descent algorithm or other model training algorithm. In particular, the LSTM model may be trained to recognize seating of the broach 14 in the bone 16 and fracture of the bone 16 based on sequences of input sensor data. Accordingly, during training the LSTM model may recognize and account for differences in technique between individual strikes on the instrument handle 12, including differences in location of impaction differences in impaction angle, and other differences. In block 430, the analysis device 120 trains a random forest (RF) predictive model/classifier based on the output from the LSTM model and the labeled sensor data. The RF model is trained to classify output from the LSTM model as unseated, seated, or fracture based on the label associated with the sensor data. The RF model may be trained using any appropriate decision tree learning algorithm.

In block 432, the system 10 determines whether model training is completed. For example, the analysis device 120 may determine whether the machine learning model has reached a certain error threshold or otherwise determine whether the machine learning model is sufficiently trained. If additional training is required, the method 400 loops back to block 402 to continue training the machine learning model. If no further training is required, the method 400 is completed. After training, the machine learning model may be used to perform inferences as described below in connection with FIG. 5.

Referring now to FIG. 5, in use, the instrument system 10 may perform a method 500 for monitoring and predicting impaction state during a surgical procedure. For example, the operations of the method 500 may be performed by one or more components of the environment 200 described above in connection with FIG. 2. The method 500 begins with block 502, in which the system 10 determines whether to monitor impaction and predict impaction state. For example, a surgeon or other operator may instruct the system 10 to start monitoring impaction using the user interface 140 or other control. If the system 10 determines to start monitoring impaction and predicting impaction state, the method 500 advances to block 504. If not, the method 500 loops back to block 502.

In block 504, the acquisition device 100 collects sensor data from one or more sensors 18, 34, and/or 36 during impaction of the broach 14 into the patient's femur 16. As described above, during an orthopaedic surgical procedure, the surgeon impacts the broach 14 into the patient's femur 16 by striking the instrument handle 12 attached to the broach 14 using the orthopaedic mallet 32. The acquisition device 100 captures sensor signals, including acceleration, vibration, and acoustic signals, as the surgeon impacts the instrument handle 12. After collecting the sensor data, the acquisition device 100 provides the sensor data to the analysis device 120 for further processing.

In some embodiments, in block 506 the acquisition device 100 receives vibration and/or audio sensor data. In the illustrative embodiment, the acquisition device 100 receives vibration data from the vibration sensor 24 coupled to the instrument handle 12 and audio data from an external audio sensor 36. Additionally or alternatively, in some embodiments the acquisition device 100 may receive audio data from an audio sensor 30 coupled to the instrument handle 12.

In some embodiments, in block 508 the acquisition device 100 receives IMU sensor data. In the illustrative embodiment, the acquisition device 100 receives IMU data (indicative of motion, including linear acceleration, angular rate, and magnetic field) from the IMU sensor 28 coupled to the instrument handle 12. Additionally or alternatively, in some embodiments the acquisition device 100 may receive IMU data from an IMU sensor coupled to the orthopaedic mallet 32.

In some embodiments, in block 510, the acquisition device 100 receives load or pressure data from the FSR/load cell 20 coupled to the instrument handle 12. In some embodiments, in block 512 the acquisition device 100 receives displacement data from the displacement sensor 26 coupled to the instrument handle 12.

In block 514, the analysis device 120 pre-processes the sensor data to prepare for input to the machine learning model. The analysis device 120 may perform one or more filtering, normalization, and/or feature extraction processes to prepare the sensor data for processing. In particular, the analysis device 120 may perform the same pre-processing operations as described above in connection with block 420 of FIG. 4. In block 516, the analysis device 120 transforms the sensor data (collected as time series data) into frequency domain data using a fast Fourier transform (FFT). Transforming to frequency domain may remove noise and allow for improved identification of peaks in the sensor data. In block 518, the analysis device 120 performs principal component analysis to reduce dimensionality of the sensor data. Reducing dimensionality may improve processing efficiency by combining and/or eliminating dependent variables in the sensor data. It should be understood that in some embodiments, the system 10 may not reduce dimensionality of the sensor data, and instead, for example, may reduce the volume of input sensor data by removing certain sensors from the system 10.

In block 520, the analysis device 120 performs a predicted impaction state inference using the trained machine learning model with the pre-processed sensor data. As described above, the machine learning model is trained to identify anomalies in the sensor data, including the broach 14 being fully seated in the femur 16 and a fracture of the femur 16. The machine learning model is further trained to classify the sensor data, based on any identified anomalies, into the unseated, seated, and fracture states. To perform the inference, in block 522 the analysis device 120 inputs the pre-processed sensor data to the LSTM model. The LSTM model outputs data that is indicative of anomalies detected and/or predicted based on the input sensor data, including seating of the broach 14 in the bone 16 and fracture of the bone 16. Output from the LSTM model may recognize anomalies regardless of any differences in technique between individual strikes on the instrument handle 12. In block 524, the analysis device 120 inputs the output from the LSTM model into the RF classifier. The RF classifier outputs a classification of the predicted impaction state as unseated, seated, or fracture.

In block 526, the analysis device 120 outputs the impaction state prediction using the user interface 140. The user interface 140 may output the impaction state using any appropriate output modality. For example, the impaction state prediction may be displayed visually using a graphical display, warning lights, or other display. As another example, the impaction state prediction may be output using an audio device as a warning sound, annunciation, or other sound. In some embodiments, in block 528 the user interface 140 may indicate whether the impaction state prediction is unseated, seated, or fracture. In some embodiments, in block 530, the user interface 140 may indicate a probability or other relative score associated with the prediction. For example, the score may indicate a relative confidence level that the broach 14 is unseated or seated, and/or a relative confidence level that a fracture exists in the femur 16. After outputting the impaction state prediction, the method 500 loops back to block 502 to continue monitoring impaction.

Figure 6:
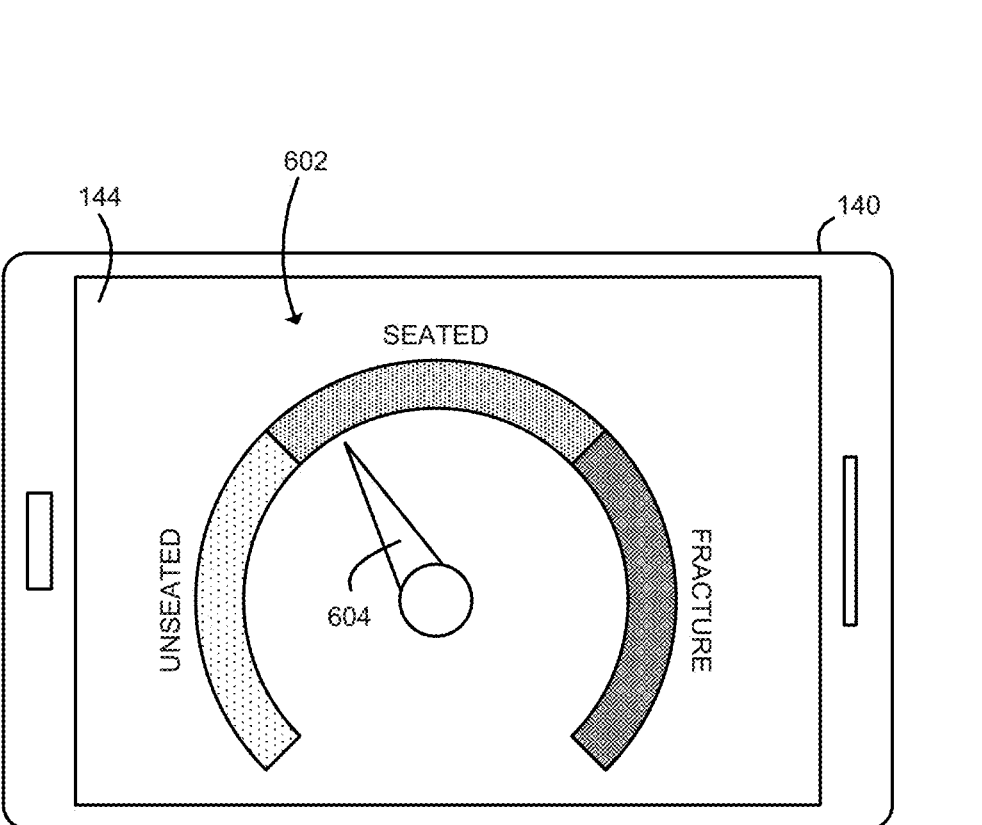
FIG. 6 is a schematic drawing of at least one embodiment of a user interface of the system of FIGS. 1-3.

Referring now to FIG. 6, diagram 600 illustrates one potential embodiment of a user interface 140. The illustrative user interface 140 is a tablet computer having a display 144. The display 144 shows a graphical representation 602 of the impaction state prediction. The illustrative graphical representation 602 includes a pointer 604 that points to the current impaction state prediction. Each of the potential impaction states includes a color-coded bar (represented as shading in FIG. 6). For example, in an embodiment the unseated state may be color-coded as yellow, the seated state may be color-coded as green, and the fracture state may be color-coded as red. In the illustrative embodiment, the pointer 604 indicates the relative score associated with the impaction state prediction by the relative position pointed to within the associated color-coded bar. In some embodiments, the graphical representation 602 may include gradations or other indications of the relative score.

Of course, other embodiments of the user interface 140 may be used. For example, in some embodiments, the user interface 140 may be included on the orthopaedic mallet 32. In those embodiments, the user interface 140 may include a set of LEDs or other indicator lights. One or more of the LEDs may be illuminated based on the predicted impaction state. For example, the user interface 140 may illuminate a yellow LED when the prediction impaction state is unseated, a green LED when the prediction impaction state is seated, and a red LED when the prediction impaction state is fracture.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method for predicting impaction state during an orthopaedic surgical procedure, the method comprising:
   collecting sensor data during the orthopaedic surgical procedure from an impaction sensor, wherein the sensor data is indicative of impaction state of an orthopaedic implement relative to a patient's bone;
   generating an impaction state prediction with a machine learning model based on the sensor data, wherein the impaction state prediction comprises an unseated state, a seated state, or a fracture state; and
   outputting the impaction state prediction.

2. The method of claim 1, wherein collecting sensor data from the impaction sensor comprises:
   collecting vibration data from a vibration sensor coupled to a surgical instrument;
   collecting motion data from an inertial measurement unit coupled to the surgical instrument; and
   collecting audio data from an external microphone.

3. The method of claim 1, wherein generating the impaction state prediction with the machine learning model based on the sensor data comprises:
   pre-processing the sensor data to generate processed sensor data; and
   inputting the processed sensor data to the machine learning model.

4. The method of claim 1, wherein generating the impaction state prediction with the machine learning model based on the sensor data comprises:

inputting the sensor data to a recurrent neural network to generate anomaly prediction data; and
   inputting the anomaly prediction data to a classifier to generate the impaction state prediction.

5. The method of claim 4, wherein the recurrent neural network comprises a long short-term memory network, and wherein the classifier comprises a random forest predictive model.

6. A method for training a machine learning model for impaction state prediction, the method comprising:
   collecting sensor data from an impaction sensor, wherein the sensor data is indicative of impaction state of an orthopaedic implement relative to a bone or bone analog;
   labelling the sensor data with an impaction state label to generate labeled sensor data, wherein the impaction state label comprises an unseated state, a seated state, or a fracture state; and
   training a machine learning model to predict impaction state for input sensor data based on the labeled sensor data.

7. The method of claim 6, wherein training the machine learning model based on the labeled sensor data comprises:
   pre-processing the labeled sensor data to generate processed sensor data; and
   training the machine learning model based on the processed sensor data.

8. The method of claim 7, wherein pre-processing the labeled sensor data comprises:
   transforming the labeled sensor data to a frequency domain to generate frequency domain sensor data; and
   reducing the dimensionality of the frequency domain sensor data to generate the processed sensor data.

9. The method of claim 8, wherein reducing the dimensionality of the frequency domain sensor data comprises performing principal component analysis of the frequency domain sensor data.

10. The method of claim 6, wherein training the machine learning model based on the labeled sensor data comprises:
   training a recurrent neural network with the labeled sensor data to identify anomalies in the labeled sensor data; and
   training a classifier with the anomalies in the labeled sensor data to predict the impaction state.

11. The method of claim 10, wherein the recurrent neural network comprises a long short-term memory network.

12. The method of claim 11, wherein the classifier comprises a random forest predictive model.

13. A method for training an impaction analyzer for an orthopaedic surgical procedure, the method comprising:
   generating, by an impaction sensor, sensor data indicative of impaction state of an orthopaedic implement relative to a bone or bone analog;
   collecting the sensor data from the impaction sensor;
   labeling the sensor data with an impaction state label to generate labeled sensor data; and
   training a machine learning model to predict impaction state for input sensor data based on the labeled sensor data.

14. The method of claim 13, wherein collecting the sensor data from the impaction sensor comprises collecting vibration data from a vibration sensor coupled to a surgical instrument.

15. The method of claim 13, wherein collecting the sensor data from the impaction sensor comprises to collecting motion data from an inertial measurement unit coupled to a surgical instrument.

16. The method of claim 13, wherein to collecting the sensor data from the impaction sensor comprises to collecting audio data from an external microphone.

17. The method of claim 13, wherein to collecting the sensor data from the impaction sensor comprises to collecting sensor data from a sensor coupled to a surgical instrument, wherein the sensor comprises a force sensing resistor, a load cell, or a displacement sensor.

18. The method of claim 13, wherein training the machine learning model based on the labeled sensor data comprises:

transforming the labeled sensor data to a frequency domain to generate frequency domain sensor data;

reducing dimensionality of the frequency domain sensor data to generate the processed sensor data; and training the machine learning model based on the processed sensor data.

19. The method of claim 18, wherein reducing the dimensionality of the frequency domain sensor data comprises performing principal component analysis of the frequency domain sensor data.

20. The method of claim 13, wherein training the machine learning model to predict impaction state for input sensor data based on the labeled sensor data comprises:

training a recurrent neural network with the labeled sensor data to identify anomalies in the labeled sensor data; and training a classifier with the anomalies in the labeled sensor data to predict the impaction state.

\*    \*    \*    \*    \*